(12) United States Patent
Ye et al.

(10) Patent No.: US 10,750,932 B1
(45) Date of Patent: Aug. 25, 2020

(54) METHOD OF ASSEMBLING ENDOSCOPE OPTICAL COMPONENTS

(71) Applicant: STERIS INSTRUMENT MANAGEMENT SERVICES, INC., Birmingham, AL (US)

(72) Inventors: Shusheng Ye, Cooper City, FL (US); Zoltan A. Bodor, Cooper City, FL (US)

(73) Assignee: STERIS Instrument Management Services, Inc., Birmingham, AL (US)

( * ) Notice: Subject to any disclaimer, the term of this patent is extended or adjusted under 35 U.S.C. 154(b) by 0 days.

(21) Appl. No.: 16/438,152

(22) Filed: Jun. 11, 2019

(51) Int. Cl.
*A61B 1/00* (2006.01)
*G02B 6/38* (2006.01)
*G02B 23/24* (2006.01)
*A61B 17/00* (2006.01)

(52) U.S. Cl.
CPC ........ *A61B 1/0011* (2013.01); *A61B 1/00096* (2013.01); *A61B 1/00163* (2013.01); *G02B 6/3849* (2013.01); *A61B 2017/00526* (2013.01); *G02B 23/2407* (2013.01)

(58) Field of Classification Search
None
See application file for complete search history.

(56) References Cited

U.S. PATENT DOCUMENTS

| | | | | |
|---|---|---|---|---|
| 4,750,476 A * | 6/1988 | Forkner | ................. | A61B 1/002 600/138 |
| 4,787,699 A * | 11/1988 | Moulin | ................. | G02B 6/3835 385/80 |
| 5,437,626 A * | 8/1995 | Cohen | ................. | A61B 1/00165 600/109 |
| 5,469,521 A * | 11/1995 | Coutts | ................. | G02B 6/3861 385/77 |
| 5,524,633 A * | 6/1996 | Heaven | ............ | A61B 17/00234 128/DIG. 24 |
| 5,643,175 A * | 7/1997 | Adair | ................. | A61B 1/00073 600/123 |
| 6,240,231 B1 * | 5/2001 | Ferrera | ................. | G02B 6/403 385/115 |
| 2008/0175548 A1 * | 7/2008 | Knecht | ................. | G02B 6/4475 385/100 |
| 2011/0034917 A1 * | 2/2011 | Brannan | ................. | A61B 18/00 606/41 |

(Continued)

*Primary Examiner* — Jerry Rahll
(74) *Attorney, Agent, or Firm* — C. Brandon Browning; Maynard, Cooper & Gale, PC

(57) ABSTRACT

An optical component assembly method including shrinking a first end of a heat shrink tube about a first optical component, inserting a loading portion of a loading tube into a second end of the heat shrink tube, radially-inserting a plurality of optical components into a staging portion of the loading tube thereby forming a line of optical components, the staging portion being seamlessly coupled to and integrally-formed with the loading portion, moving the line of optical components from the staging portion into the loading portion, and removing the loading portion from between the line of optical components and the heat shrink tube thereby depositing the line of optical components in the heat shrink tube. The line of optical components is fixed and optically aligned within the heat shrink tube by applying radial pressure, axial pressure and heat to the line of optical components simultaneously.

20 Claims, 7 Drawing Sheets

(56) References Cited

U.S. PATENT DOCUMENTS

| | | | |
|---|---|---|---|
| 2016/0223764 A1* | 8/2016 | Cervantes | G02B 6/3889 |
| 2018/0078279 A1* | 3/2018 | Germain | A61B 17/32002 |
| 2018/0228346 A1* | 8/2018 | Sekowski | A61B 1/05 |
| 2019/0059709 A1* | 2/2019 | Ting | A61B 1/051 |

* cited by examiner

METHOD OF ASSEMBLING ENDOSCOPE OPTICAL COMPONENTS

FIELD OF THE INVENTION

The present invention is directed to a method of assembling an optical relay system, and more particularly, to a method and apparatus for assembling an endoscopic optical relay system within a flexible, shrinkable tube.

BACKGROUND OF THE INVENTION

The assembly of optical relay systems within flexible tubes is known in the art. For example, U.S. Pat. No. 7,530,945 to Rudischhauser et al. describes a method for assembling an endoscope having an optical system with several components that are at least partially surrounded by a tube made of both a transparent and a shrunk material. The method includes introducing the optical components into the tube of transparent and shrinkable material to form a unit, followed by shrinking the shrinkable material of the tube for fixing the position of the components contained within the tube relative to one another. To ensure the proper positioning of the components relative to one another, the components are inspected through the transparent shrunk material of the shrunk tube. After proper positioning of the components is confirmed, the unit composed of the shrunk tube and the components contained therein is introduced into a tubular shaft of the endoscope.

U.S. Pat. No. 8,819,913 to Bodor et al. describes a method of assembling an optical relay system including forming a line of optical components within an optical component aligning groove of a first base member, axially aligning a cylinder with the aligning groove of the first base member, detachably coupling the cylinder to the first base member and directing the line of optical components from the optical component receiving groove into the cylinder. The cylinder, the line of optical components and a shrinkable tube which has previously been placed around the cylinder are then detached from the first base member and positioned within a cylinder receiving groove of a second base member. With axial movement of the cylinder restricted within the cylinder receiving groove, the line of optical components is pushed out the cylinder and into the shrinkable tube which slides off of the cylinder by virtue of its constriction about a distal end of the line of optical components. The line of optical components and shrinkable tube then are advanced along the cylinder receiving groove and through a heating area where the shrinkable tube is shrunk about the line of optical components. To ensure axial compression upon the line of optical components within the shrinkable tube, a tension device located upstream of the heating area applies pressure on the shrink tube as it and the line of optical components are advanced long the cylinder receiving groove thereby causing the tube to stretch axially while the shrinkable tube is heated and shrunk radially about the line of optics.

SUMMARY OF THE INVENTION

The present invention is directed to a method of assembling an optical system. According to one aspect of the invention, the method includes shrinking a first end of a heat shrink tube about a first optical component, inserting a loading portion of a loading tube into a second end of the heat shrink tube, placing a plurality of optical component in a staging portion of the loading tube thereby forming a line of optical components, the staging portion having an open radial portion, moving the line of optical components from the staging portion into the loading portion, and removing the loading portion from between the line of optical components and the heat shrink tube thereby depositing the line of optical components in the heat shrink tube.

In one embodiment, the plurality of optical components are radially placed in the staging portion of the loading tube by lowering them into the staging portion through the open radial portion. In another embodiment, the loading tube is removed from between the line of optical components and the heat shrink tube by pushing the line of optical components against the first optical component and out of the loading tube thereby causing the heat shrink tube to slide off of the loading portion of the loading tube. In another embodiment, a portion of the first optical component extends out of the heat shrink tube. In another embodiment, the line of optical components is misaligned radially and includes a gap between at least two optical components of the plurality of optical components. In yet another embodiment, the a second optical component of the plurality of optical components is fixed in the second end of the heat shrink tube with a portion of the second optical component extending out of the heat shrink tube.

According to another aspect of the invention, there is provided a method for assembling an optical relay system, the method including shrinking a first end of a heat shrink tube about a first optical component, inserting a loading tube into a second end of the heat shrink tube, placing a plurality of optical components in the loading tube thereby forming a line of optical components, and removing the loading tube from between the line of optical components and the heat shrink tube thereby depositing the line of optical components in the heat shrink tube. Thereafter, the line of optical components is fixed and optically aligned within the heat shrink tube by simultaneously applying radial pressure, axial pressure and heat to the line of optical components.

In one embodiment, the line of optical components are fixed and optically aligned in the heat shrink tube by heating the heat shrink tube and line of optical components while positioned in a V-groove with an elongate weight resting on top of the heat shrink tube and the line of optical components pressed between a pair of opposing, biased plungers. In this manner, heat, radial pressure and axial pressure are simultaneously applied to the line of optical components which ensures both radial and axial alignment of the line of optical components. According to another embodiment of the invention, the plurality of optical components is placed in the loading tube by radially-inserting the plurality of optical components into a staging portion of the loading tube. According to another embodiment of the invention, the alignment and order of the plurality of optical components are observed in the staging portion through an opening in a sidewall of the loading tube. According to yet another embodiment of the invention, the staging portion as a length that is defined by a length of an opening formed in a sidewall of the loading tube.

According to another aspect of the invention, there is provided a method for assembling an optical relay system including providing a loading member having a tubular loading portion and a staging portion that is seamlessly coupled to the tubular loading portion, forming a line of optical components in the staging portion by radially-inserting a plurality of optical components into the staging portion, inserting the loading portion into a heat shrink tube, and removing the loading portion from between the line of optical components and the heat shrink tube thereby depositing the line of optical components in the heat shrink tube.

In one embodiment of the invention, the line of optical components may be fixed and optically aligned within the heat shrink tube by applying radial pressure, axial pressure and heat simultaneously to the line of optical components. In another embodiment of the invention, the heath shrink tube and line of optical components may be located in a groove when the radial pressure is applied to the line of optical components, wherein the groove contacts each optical component of the line of optical components along two spaced-apart lengths of the optical component. In another embodiment, the loading portion may be removed from between the line of optical components and the heat shrink tube by pushing the line of optical components out of the loading portion with a push rod, wherein the push rod includes an arm that extends radially and travels axially through a radial opening in a sidewall of the staging portion as the push rod pushes the line of optical components out of the loading portion. In yet another embodiment of the invention, the heat shrink tube is selected from an opaque tube for preventing light from passing through the heat shrink tube or a translucent or transparent tube for allowing the alignment of the line of optical components to be seen through the heat shrink tube.

DETAILED DESCRIPTION OF THE INVENTION

The present invention is directed to a method for assembling an endoscopic optical relay. Generally, the method includes shrinking a first end of a heat shrink tube 10 about a first optical component, inserting a loading portion 12 of a loading tube 14 into a second end of heat shrink tube 10, radially-inserting a plurality of optical components into a staging portion 16 of loading tube 14 thereby forming a line of optical components, the staging portion being seamlessly coupled to and integrally-formed with loading portion 12, moving the line of optical components from staging portion 16 into loading portion 12, and removing loading portion 12 from between the line of optical components and heat shrink tube 10 thereby depositing the line of optical components in heat shrink tube 10. The line of optical components is fixed and optically aligned within heat shrink tube 10 by applying radial pressure, axial pressure and heat to the line of optical components simultaneously.

Figure 1:
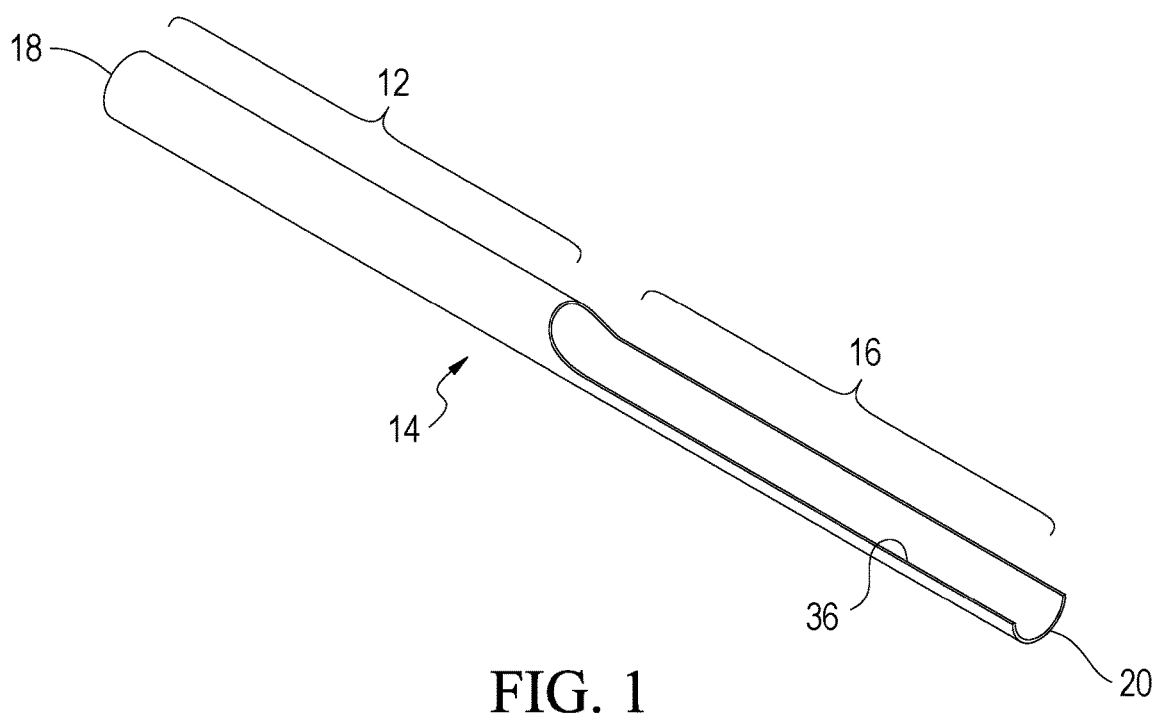
FIG. 1 is a perspective view of a loading tube in accordance with the present invention.
Figure 2:
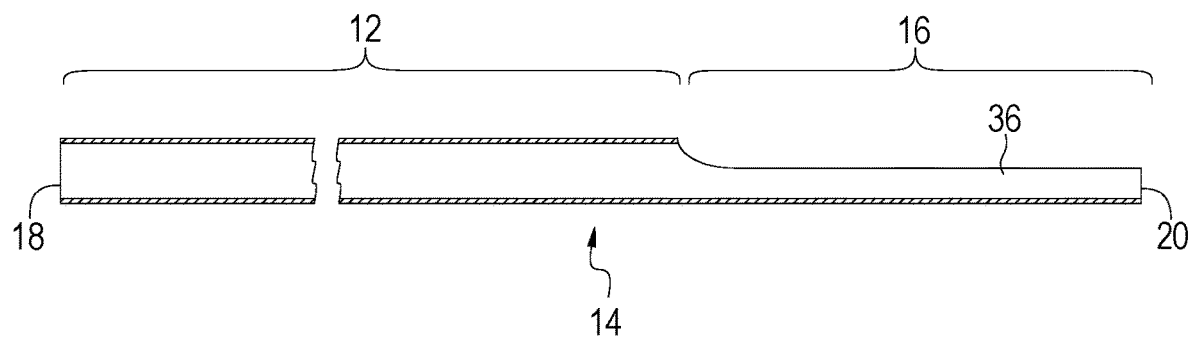
FIG. 2 is a sectional view of the loading tube of FIG. 1 taken along a length of the loading tube.

More particularly, as depicted in FIGS. 1 and 2, loading tube includes a first end 18 and an opposing second end 20. First end 18 has a first opening therethrough defined by a continuous sidewall that extends towards second end 20 to form loading portion 12. Second end 20 is formed by a semi-circular sidewall that extends towards first end 22 to form staging portion 16. The semi-circular sidewall is formed by removing a semi-circular portion from the cylinder. Staging portion 16 has a length sufficient to contain a complete endoscopic relay system. Though loading tube 14 is shown in FIGS. 1 and 2 as having a round cross-section and thus constructed from a cylinder, it is understood that the tube from which loading tube 14 is constructed may have a square, triangular, hexagonal, heptagonal, decagonal, nonagonal or other cross-section. Loading tube 14 is constructed from a seamless tube fabricated from plastic, metal, ceramic, wood, or any other suitable material.

Figure 3:
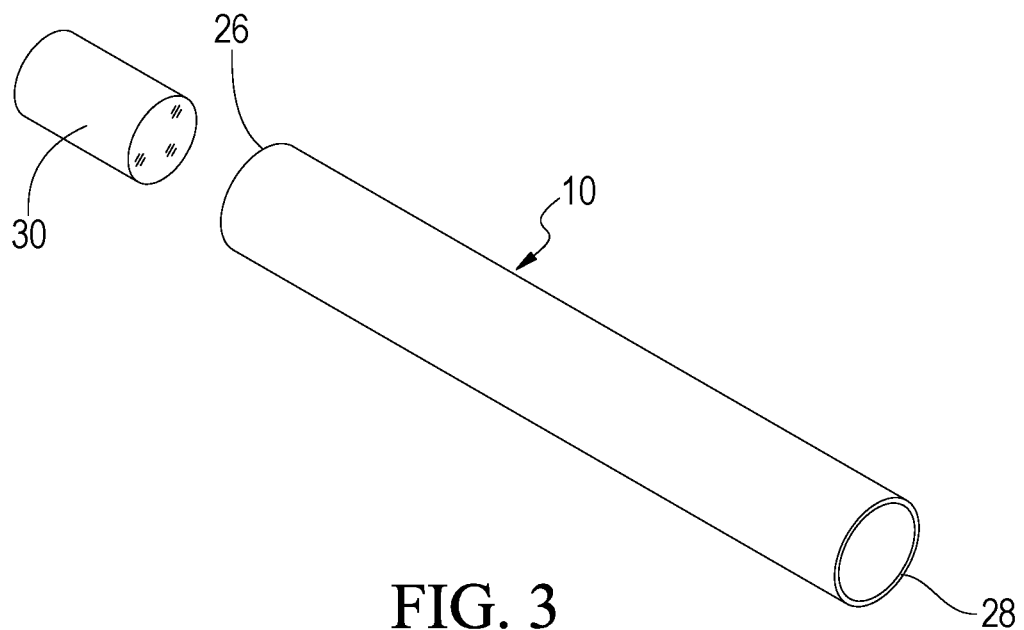
FIG. 3 is a perspective view of a heat shrink tube in accordance with the present invention.

Referring to FIG. 3, heat shrink tube 10 is constructed from a thin, flexible, heat-shrinkable plastic cylinder. Heat shrink tube 10 includes a first end 26, an opposing second end 28 and a continuous sidewall extending there between. Heat shrink tube 10 has an inner diameter that is slightly greater than an outer diameter of loading portion 12 of loading tube 14.

Figure 4:
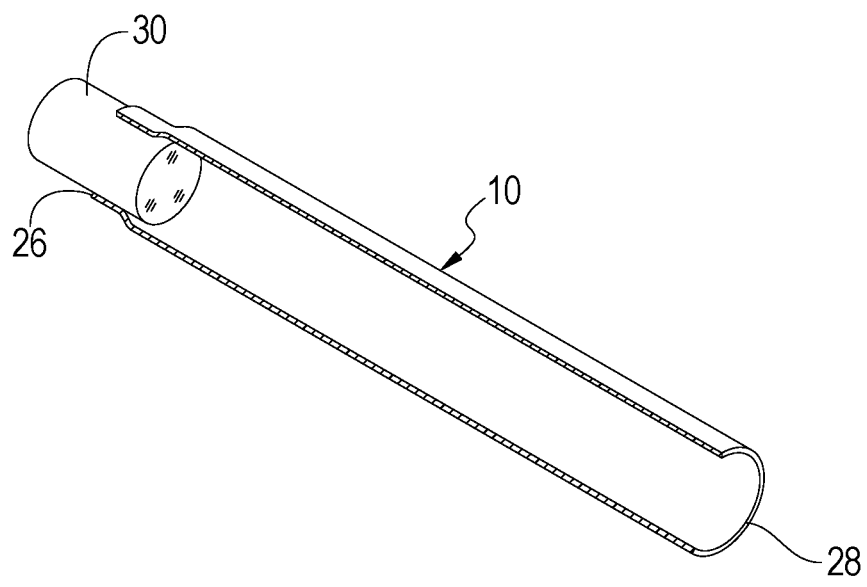
FIG. 4 is a partial sectional view of the heat shrink tube of FIG. 3 fixed at one end thereof about an optical component.

As illustrated in FIG. 4, a first optical component 30 such as a rod lens is fixed within first end 26 of heat shrink tube 10. This occurs by manually inserting first optical component 30 partially within first end 26 and heating first end 26 using a heat source to shrink only that portion of heat shrink tube 10 that is immediately adjacent to the radial surface of first optical component 30. Although first optical component 30 is shown to partially extend out of tube 10, it is understood that first optical component 30 may be entirely enclosed within first end 26 of heat shrink tube 10.

Figure 5:
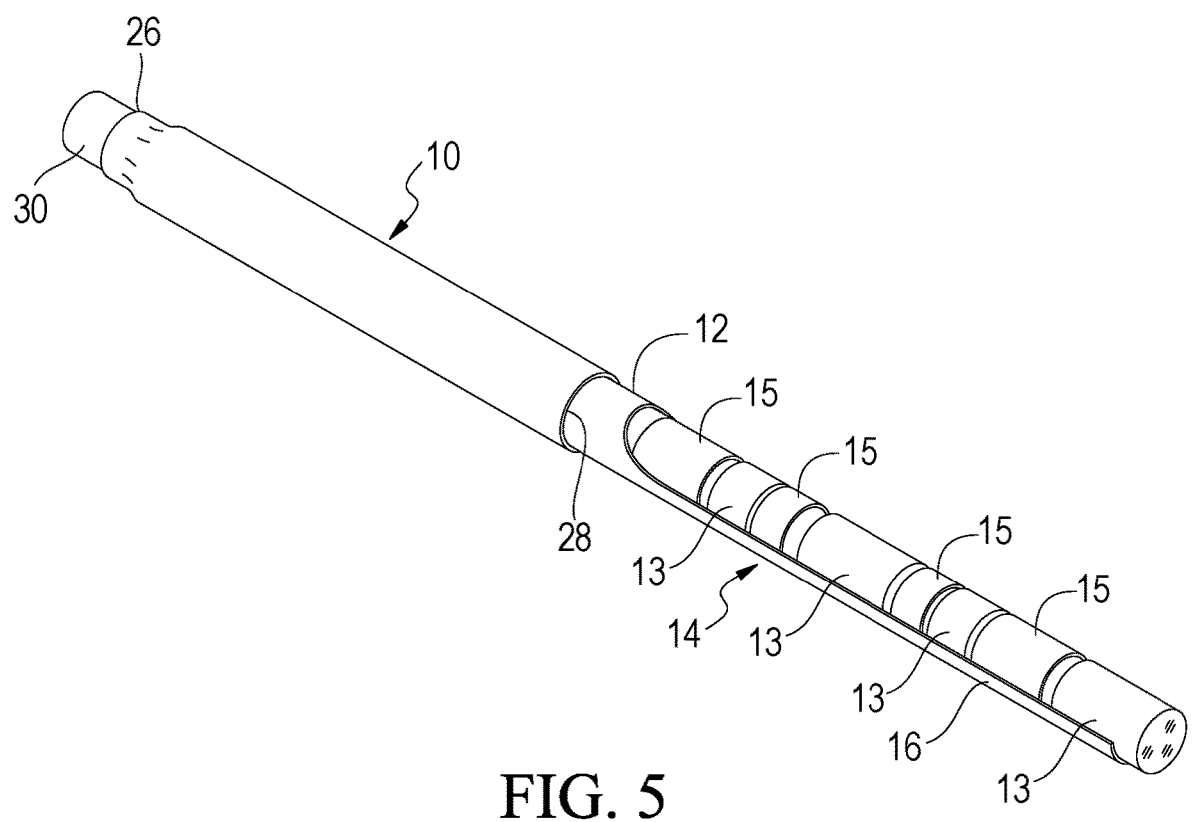
FIG. 5 is a perspective view of the loading tube of FIG. 1 showing the heat shrink tube of FIG. 4 inserted over a loading portion of the loading tube with a plurality of the optical components arranged in a line within the staging portion.

Referring to FIG. 5, after first optical component 30 is fixed within heat shrink tube 10, first end 18 of loading portion 12 of loading tube 14 is inserted through second end 28 of heat shrink tube 10 with first end 18 of loading tube 14 pressed against first optical component 30. Thereafter, a plurality of optical components, which may consist of rod lenses 13, spacers 15, aperture stops and/or other optical components, are manually placed into staging portion 16 in an order, i.e., proximal to distal, required for constructing the desired optical relay assembly. Because the plurality of optical components can be placed radially into staging portion 16, there is no requirement that the components be placed into the staging portion in any particular sequence.

Thus, for example, lens 13 extending out of second end 20, as depicted in FIG. 5, may be placed in staging portion 16 before the spacer 13 arranged immediately adjacent to such lens 13, since there is no requirement that the plurality of optical components be inserted axially through an end of loading tube 14.

Figure 6A:
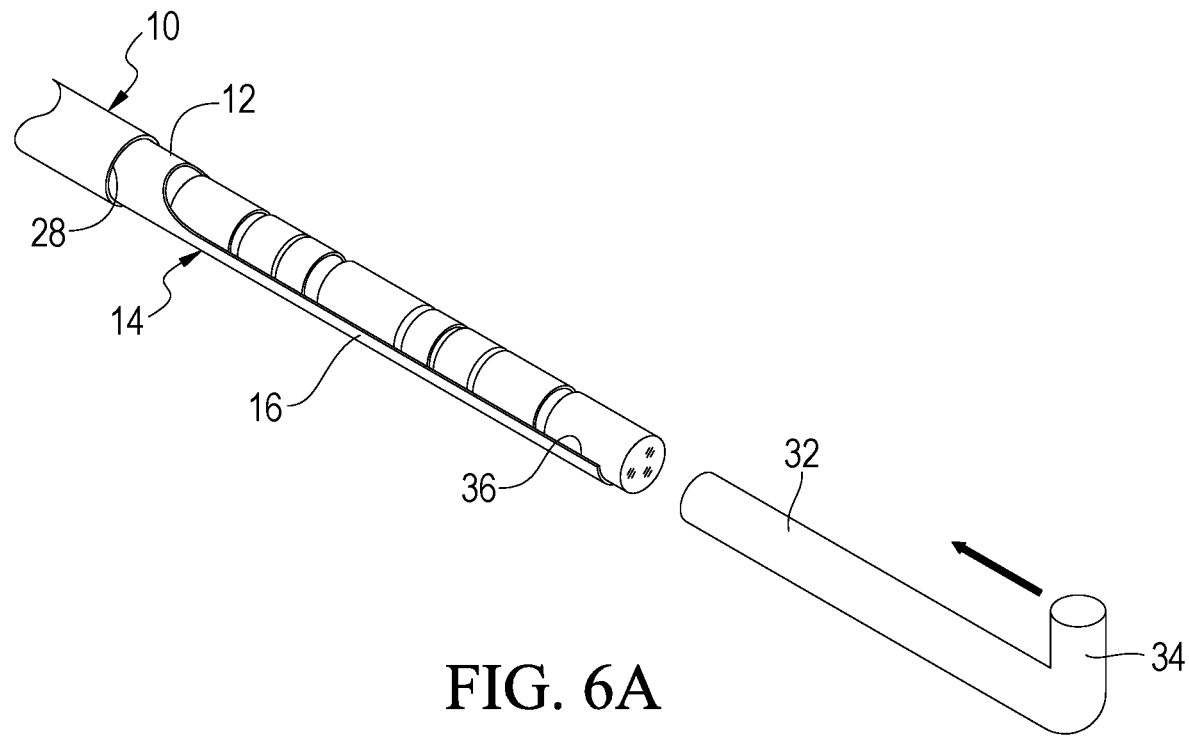
FIGS. 6A and 6B are perspective views of the loading tube of FIG. 1 showing the line of optical components of FIG. 5 being moved from the staging portion into the loading portion.
Figure 6B:
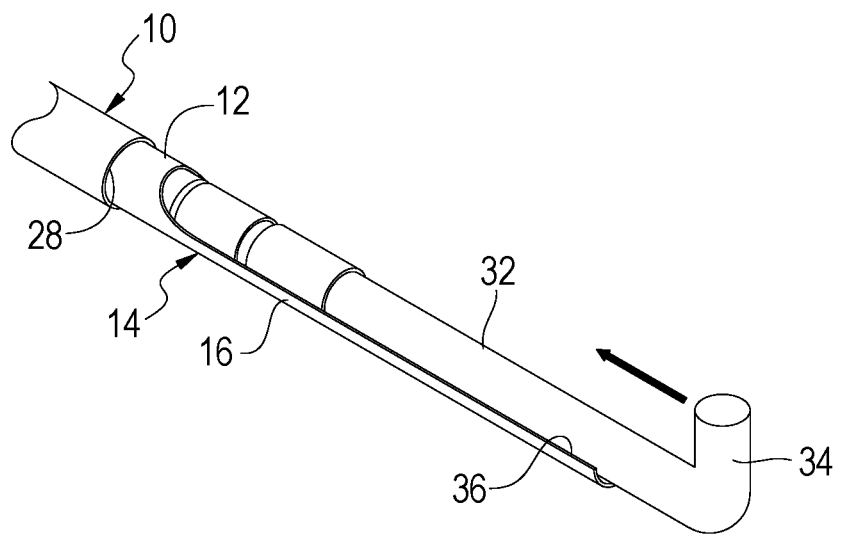
Figure 7:
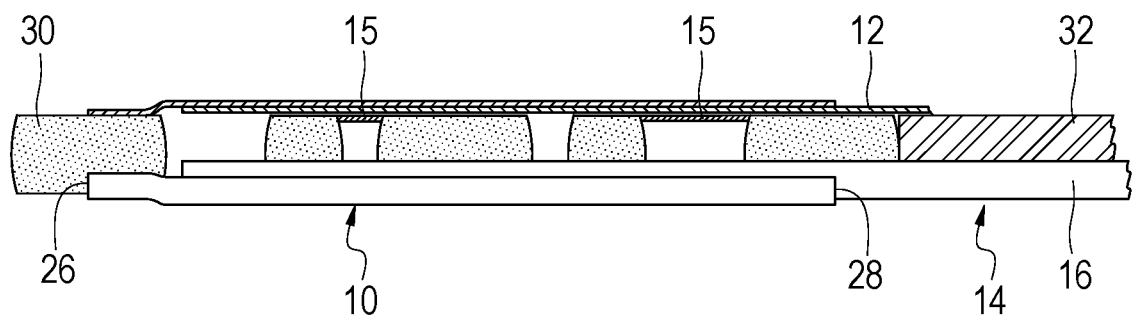
FIG. 7 is a sectional view of the loading tube of FIG. 1 taken along the length of the loading tube showing the line of optical components of FIG. 5 being moved from the staging portion into the loading portion.

Once the plurality of optical components is in place thereby forming a line of optical components in staging portion 16, a push rod 32 is pressed against the end of the line of optical components, as shown in FIGS. 6A and 6B, towards first optical components 30 thereby forcing the line of optical components to slide as a continuous unit out of staging portion 16 and into loading portion 12. As push rod 32 pushes the line of optical components through staging portion 16 and into loading portion 12, a radially extending handle 34 of the push rod extends radially outward and travels axially through a radial opening defined by a sidewall 36 of staging portion 16.

Figure 8:
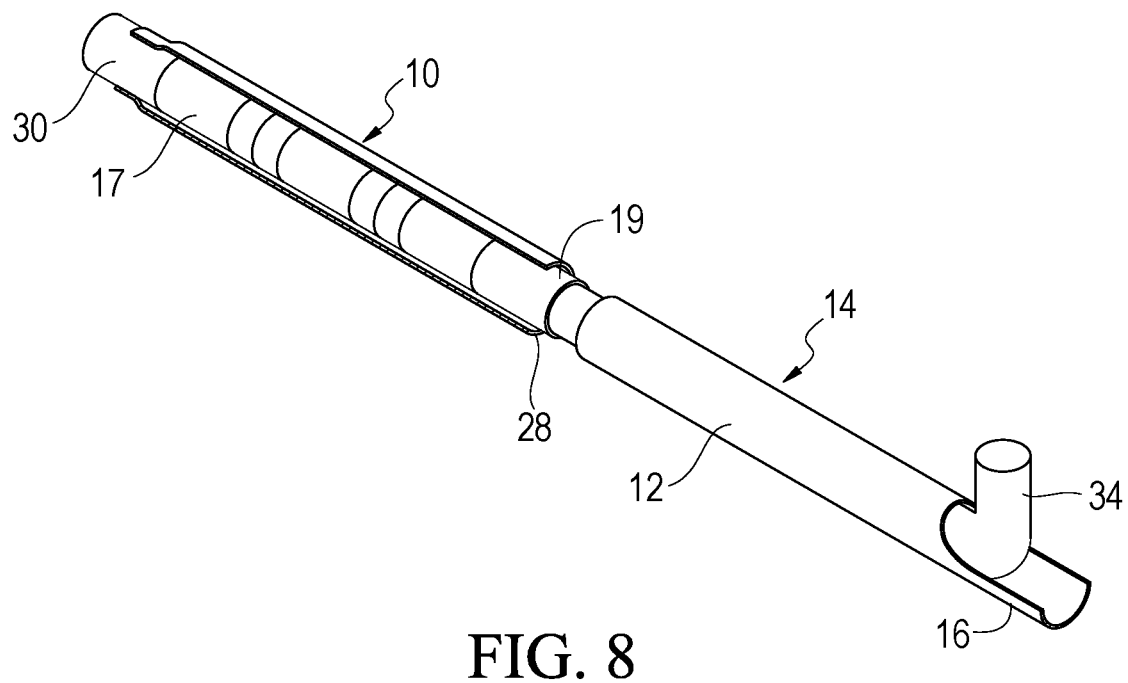
FIG. 8 is a perspective view of the loading tube of FIG. 1 showing a line of optical components being deposited within the heat shrink tube of FIG. 4.
Figure 9:
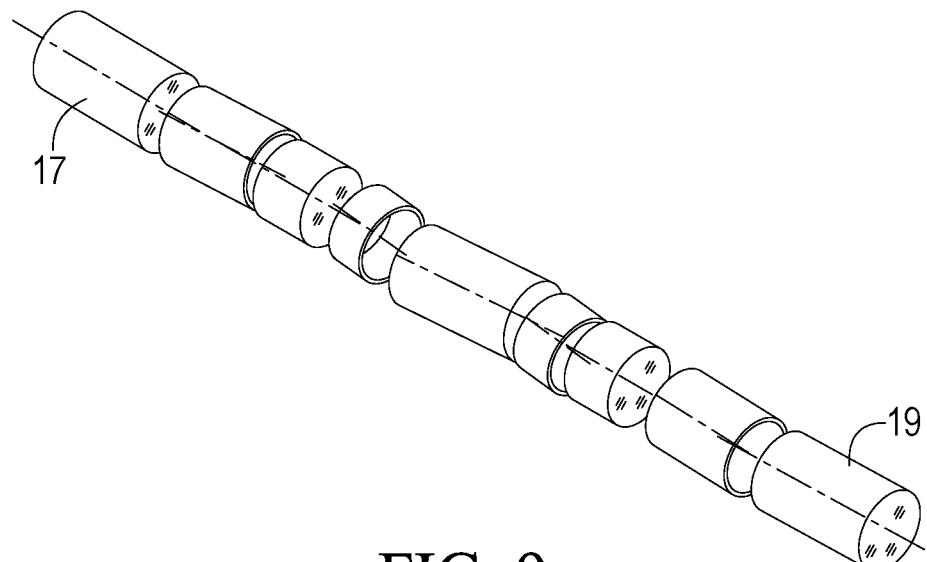
FIG. 9 is a partial sectional view of a line of optical components positioned within the heat shrink tube of FIG. 4 showing axial and radial misalignment of the optical components in the heat shrink tube.

As depicted in FIG. 8, a leading optical component 17 of the line of optical components slides through loading portion 12 and eventually directly contacts first optical component 30. As the line of optical components is further pressed against first optical component 30, heat shrink tube 10 is caused to slide off loading portion 12 of loading tube 14 with the line of optical components deposited within heat shrink tube 10. This occurs with no stretching or minimal stretching of tube 10. As illustrated in FIGS. 8 and 9, the line of optical components has a length sufficient to cause a trailing optical component 19 of the line of optical component to extend out of second end 28 of heat shrink tube 10. Furthermore, the line of optical components when fully deposited within heat shrink tube 10 are axially and radially misaligned and include spaces between the various optical components.

Figure 10:
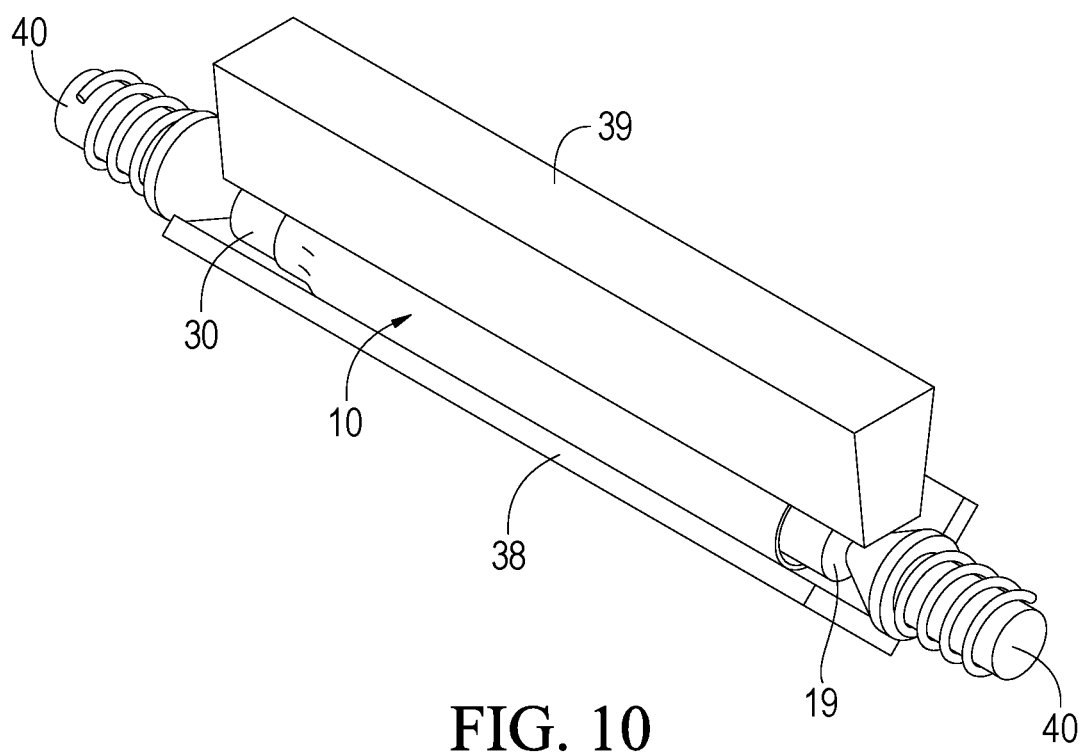
FIG. 10 is a perspective view of the heat shrink tube and line of optical components of FIG. 9 showing a weight placed on the heat shrink tube for radially and axially aligning the optical components, with the line of optical components pressed between a pair of spring loaded plungers for removing gaps between the optical components.
Figure 11:
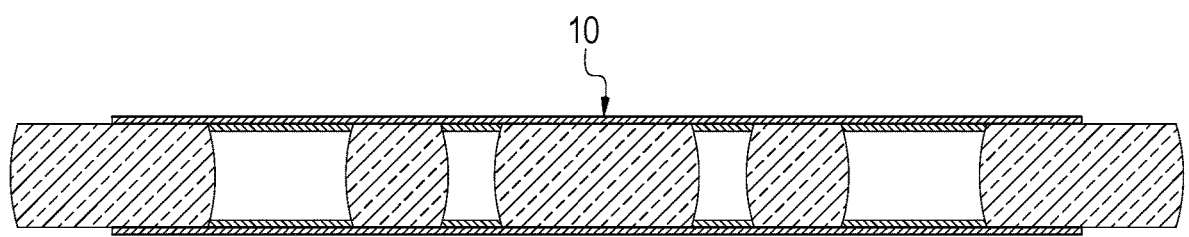
FIG. 11 is a sectional view of a line of optical components fixed with a shrunk heat shrink tube with the line optical components optically aligned and arranged as a contiguous unit in the tube.

Referring to FIG. 10, to optically align the line of optical components within heat shrink tube 10, heat shrink tube 10 is placed within a V-shaped groove of an elongate base member 38 and pressure is applied axially and radially to the heat shrink tube while simultaneously heating tube 10. In particular, an elongate weight 39 is placed on a top surface of heat shrink tube 10, while the tube is in the V-groove, and a pair of opposing spring-loaded plungers 40 are arranged to press against first optical component 30 and trailing optical component 19 of the line of optical components, respectively. The pressure exerted by weight 39 on heat shrink tube 10 forces the line of optical components into radial and axial alignment, while opposing plungers 40 force the line of optical components into a contiguous unit with no spacing between the optical components. Arranged in this manner, heat shrink tube 10 and the contiguous and optically aligned line of optical components are heated, for example, in an oven. Heating causes heat shrink tube 10 to shrink both axially and radially thereby pressing the line of optical components together both axially and radially. As depicted in FIG. 12, following heating of heat shrink tube 10, the line of optical components are axially and radially aligned within tube 10 with no spaces between the optical components thereby forming a functional optical relay system for use in an endoscope.

As will be apparent to one skilled in the art, various modifications can be made within the scope of the aforesaid description. Such modifications being within the ability of one skilled in the art form a part of the present invention and are embraced by the claims below.

It is claimed:

1. A method for assembling an optical relay system comprising:
    shrinking a first end of a heat shrink tube about a first optical component,
    inserting a loading portion of a loading tube into a second end of the heat shrink tube,
    placing a plurality of optical components in a staging portion of the loading tube thereby forming a line of optical components, the staging portion having an open radial portion,
    moving the line of optical components from the staging portion into the loading portion, and
    removing the loading portion from between the line of optical components and the heat shrink tube thereby depositing the line of optical components in the heat shrink tube.

2. The method of claim 1 including placing the heat shrink tube and the line of optical components in a V-groove.

3. The method of claim 2 including placing an elongate weight on top of the heat shrink tube and the line of optical components for applying radial pressure to the line of optical components.

4. The method of claim 2 including applying axial pressure to the line of optical components using a pair of opposing, biased plungers.

5. The method of claim 1 including fixing the line of optical components within the heat shrink tube with the line of optical components optically aligned by simultaneously applying radial pressure to the line of optical components, axial pressure to the line of optical components and heat.

6. The method of claim 1 including shrinking the heat shrink tube about the first optical element by applying heat only to the first end of the heat shrink tube.

7. The method of claim 1 including placing the plurality of optical components in the staging portion of the loading tube by lowering them into the staging portion through the open radial portion.

8. The method of claim 1 including removing the loading tube from between the line of optical components and the heat shrink tube by pushing the line of optical components against the first optical component and out of the loading tube thereby causing the heat shrink tube to slide off of the loading portion of the loading tube.

9. The method of claim 1 wherein a portion of the first optical component extends out of the heat shrink tube.

10. The method of claim 1 wherein the line of optical components is misaligned radially and axially and includes a gap between at least two optical components of the plurality of optical components.

11. The method of claim 1 including fixing a second optical component of the plurality of optical components in the second end of the heat shrink tube with a portion of the second optical component extending out of the heat shrink tube.

12. A method for assembling an optical relay system comprising:
    shrinking a first end of a heat shrink tube about a first optical component,
    inserting a loading tube into a second end of the heat shrink tube,
    placing a plurality of optical components in the loading tube thereby forming a line of optical components,
    removing the loading tube from between the line of optical components and the heat shrink tube thereby depositing the line of optical components in the heat shrink tube, and
    fixing the line of optical components within the heat shrink tube with the line of optical components optically aligned by applying radial pressure, axial pressure and heat to the line of optical components.

13. The method of claim 12 including applying radial pressure to the line of optical components by placing an elongate weight on the heat shrink tube and the line of optical components and applying axial pressure to the line of optical components using a pair of opposing, biased plungers.

14. The method of claim 12 including placing the plurality of optical components in the loading tube by radially-inserting the plurality of optical components into a staging portion of the loading tube.

15. The method of claim 14 including observing the alignment and order of the plurality of optical components in the staging portion through an opening in a sidewall of the loading tube.

16. The method of claim 14 including providing the staging portion with a length that is defined by a length of an opening formed in a sidewall of the loading tube.

17. A method for assembling an optical relay system comprising:
providing a loading member having a tubular loading portion and a staging portion that is seamlessly coupled to the tubular loading portion,
forming a line of optical components in the staging portion by radially-inserting a plurality of optical components in the staging portion,
inserting the loading portion into a heat shrink tube, and
removing the loading portion from between the line of optical components and the heat shrink tube thereby depositing the line of optical components in the heat shrink tube.

18. The method of claim 17 including fixing the line of optical components within the heat shrink tube with the line of optical components optically aligned by applying radial pressure, axial pressure and heat to the line of optical components.

19. The method of claim 18 wherein the heath shrink tube and the line of optical components are located in a groove when the radial pressure is applied to the line of optical components, wherein the groove contacts each optical component of the line of optical components along two spaced-apart lengths of the optical component.

20. The method of claim 17 including removing the loading portion from between the line of optical components and the heat shrink tube by pushing the line of optical components into and out of the loading portion with a push rod, wherein the push rod includes an arm that extends through a radial opening in a sidewall of the staging portion as the push rod is pushing the line of optical components out of the loading portion.

* * * * *